United States Patent [19]
Fujiwara et al.

[11] Patent Number: 6,136,584
[45] Date of Patent: Oct. 24, 2000

[54] FK506-BINDING PROTEIN GENE

[75] Inventors: Tsutomu Fujiwara, Naruto; Shiro Okuno, Tokushima; Hisanobu Hirano, Tokushima-ken; Sadahito Shin, deceased, late of Tokushima-ken, all of Japan, by Sadae Shin, legal representative, Ken Koo Shin, Jun Na Shin, heirs

[73] Assignee: Otsuka Pharmaceutical Co., Ltd., Tokyo, Japan

[21] Appl. No.: 08/714,071

[22] PCT Filed: Mar. 9, 1995

[86] PCT No.: PCT/JP95/00393

§ 371 Date: Jul. 15, 1998

§ 102(e) Date: Jul. 15, 1998

[87] PCT Pub. No.: WO95/24480

PCT Pub. Date: Sep. 14, 1995

[30] Foreign Application Priority Data

Mar. 10, 1994 [JP] Japan .................................. 6-067967

[51] Int. Cl.[7] ..................................................... C12N 9/90
[52] U.S. Cl. ............................................................. 435/233
[58] Field of Search .............................................. 435/233

[56] References Cited

U.S. PATENT DOCUMENTS 5,457,182  10/1995  Wiederrecht et al. ................... 435/233

FOREIGN PATENT DOCUMENTS

WO 95/21861  8/1995  WIPO .

OTHER PUBLICATIONS

Rosborough, S.L., et al., "Identification of FKBP–Related Proteins with Antibodies of Predetermined Specificity and Isolation by FK 506 Affinity Chromatography", Transplantation Proceedings, vol. 23, No. 6, pp. 2890–2893, (Dec. 1991).

Sewell, Tonya J. et al., "Inhibition of Calcineurin by a Novel FK–506–binding Protein", *Journal of Biological Chemistry*, vol. 269, No. 33, pp. 21094–21102, (Aug. 19, 1994).

*Primary Examiner*—Robert A. Wax
*Attorney, Agent, or Firm*—Sughrue, Mion, Zinn, Macpeak & Seas, PLLC

[57] ABSTRACT

The present invention provides an FK506 binding protein gene containing a base sequence coding for the amino acid sequence shown under SEQ ID NO:1, in particular such a FK506 binding protein gene containing the base sequence shown under SEQ ID NO:2, a method of producing a recombinant FK506 binding protein through expression of such gene, and the recombinant protein thus produced.

The use of the gene of the present invention enables FK506 binding protein expression, and the protein is useful particularly in elucidating the mechanism of immunosuppression in living bodies or in developing or screening out therapeutic agents for autoimmune diseases (e.g. rheumatism, SLE, etc.), among others.

10 Claims, 5 Drawing Sheets

FK506-BINDING PROTEIN GENE

TECHNICAL FIELD

The present invention relates to an FK506 binding protein gene.

BACKGROUND ART

FK506 is a potent immunosuppressant and, like cyclosporin A [Borel, J. G. et al., Agents and Actions, 6, 468–471 (1976)], it is often used for preventing allograft rejection [Thomson, A. W., Immunol. Today, 10, 6–9 (1989)]. It is considered that the mechanism of its immunosuppresant action is in focus on the suppression of translation, during T cell activation [Tocci, M. et al., J. Immunol., 143, 718–726 (1989)], of a series of lymphokine genes which is critical to early immune responses. However, the precise mechanism remains unclear.

Recently, an AF506 binding protein was found in human T cells. It was identified as the 12 kDa cytosolic receptor of FK506 and shown to have peptidylprolyl cistrans isomerase activity (PPIase activity) [Siekier, J. et al., J. Immunol., 143, 1580–1583 (1989)].

Subsequently, on the basis of its amino acid sequence, a number of FK506 binding proteins (FKBPs) and corresponding cDNA clones have been isolated and the nucleotide sequences of said clones have been determined [for example, human FKBPs such as FKBP-12 (Standaert, R. F. et al., Nature, 346, 671–674 (1990); Maki, N, et al., Proc. Natl. Acad. Sci. USA, 87, 5440–5443 (1990)), FKBP-13 (Jin, Y. et al., Proc. Natl. Acad. Sci. USA, 88, 6677–6681 (1991)), FKBP-25 (Wiederrecht, G. et al., Biochem. Biophys. Res. Comm., 185, 298–303 (1992)) and FKBP-52 (Peattie, D. A. et al., Proc. Natl. Acad. Sci. USA, 89, 10974–10978 (1992)) as well as murine FKBP (Nelson, P. A. et al., Gene, 109, 255–258 (1991)), bovine FKBP (Mozier, N. M. et al., Eur. J. Biochem., 194, 19–23 (1990)), yeast FKBP (Heitman, J. et al., Proc. Natl. Acad. Sci. USA, 88, 1948–1952 (1991)), *Neurospora crassa* FKBP (Tropschug, M. et al., Nature, 346, 674–677 (1990)), *Neisseria meningitis* FKBP (Sampson, B. A. et al., Proc. Natl. Acad. Sci. USA, 89, 1164–1168 (1992)), etc.].

The above-mentioned FKBPs all have PPIase activity, which is presumably essential for protein folding during protein synthesis in cells [Ficher, G. et al., Biomed. Biochim. Acta, 43, 1101–1111 (1984)]. Although no clear evidence is available to prove that said PPIase activity is necessary for T cell activation, binding of FK506 to FKBPs is believed to bring about inhibition of PPIase activity and thereby inactivate T cells [Tropschug, M. et al., Nature, 346, 674–677 (1990)].

DISCLOSURE OF THE INVENTION

Accordingly, it is an object of the present invention to provide a novel FK506 binding protein (FKBP) gene, more particularly a novel FKBP gene which is highly homologous to the above-mentioned human FKBP-12 and whose expression product protein has high PPIase activity.

As a result of their intensive investigations, the present inventors succeeded in isolating, from a human fetal brain cDNA library, a novel gene coding for a protein highly homologous to the human FK506 binding protein 12 kD (FKBP-12) and in determining its full-length cDNA sequence. Based on these results, they have now attained the present invention.

Thus, the present invention is directed to an FK506 binding protein gene coding for an amino acid sequence defined by the sequence shown under SEQ ID NO:1 or SEQ ID NO:2 in the sequence listing.

The abbreviations for amino acids, peptides, base sequences, nucleic acids and so forth as used herein in the present specification are those recommended by the International Union of Pure and Applied Chemistry (IUPAC) and the International Union of Biochemistry (IUB) and in the "Guidelines for drafting patent specifications relative to base sequences and/or amino acid sequences" edited by the Japanese Patent Office or those commonly used in the relevant field of art.

The gene of the present invention includes genes characterized in that they comprise an open reading frame consisting of a 324 nucleic acid sequence coding for the 108 amino acid residues as shown under the above-mentioned SEQ ID NO:1.

The gene of the present invention also includes genes characterized in that they comprise an open reading frame consisting of a 240 nucleic acid sequence coding for the 80 amino acid residues as shown under the above-mentioned SEQ ID NO:2.

The novel FK506 binding proteins encoded by the genes of the present invention are characterized by high PPIase activity.

Although the gene of the present invention is represented by a single-stranded DNA sequence, as shown under, for example, SEQ ID NO:3, the present invention also includes the DNA sequence complementary to such a single-stranded DNA sequence as well as a component comprising both of these. The DNA sequence representing the gene of the present invention shown in the above-mentioned SEQ ID NO:3 is an example of the codon combination coding for the respective amino acid residues according to the amino acid sequence shown under the above-mentioned SEQ ID NO:1. The gene of the present invention is not limited to the above-mentioned one but may, of course, have any other DNA base sequence comprising a combination of codons arbitrarily selected for the respective amino acid residues without altering the above-mentioned amino acid sequence. Selection of said codons can be carried out by the conventional method in which the codon usage or codon choice in the host to be used for gene recombination is taken into consideration [Nucl. Acids Res., 9, 43–74 (1981)], and these codons can be produced, for example by chemical synthesis, etc.

The gene of the present invention further includes DNA sequences coding for those equivalents to the above-mentioned amino acid sequence that are derived from the latter by deletion, addition or like modification of one or more amino acid residues or part of the amino acid sequence and have similar PPIase activity to that of the FK 506 binding protein. While production, alteration (mutation) or the like of these polypeptides may occur spontaneously, they can also be produced by posttranslational modification. Furthermore, any desired gene can be produced by gene engineering techniques such as the site-specific mutagenesis technique in which the natural gene (gene of the present invention) is altered, by a chemical synthesis technique such as the phosphite triester method in which mutant DNAs are synthesized or by combining both procedures.

By utilizing the gene of the present invention, namely by incorporating the same into a vector for use with a microorganism, for instance, and cultivating the transformant microorganism, the FK506 binding protein can be expressed readily and in large quantities, and said protein can be isolated and provided. Since said protein has PPIase activity, it is effective for various pharmacological purposes, not to speak of T cell activation, and it is also useful, among others, in elucidating the pathogenesises, the pathologies or the like of various diseases. More specifically, since the recombinant FK506 binding protein obtained by utilizing the gene of the present invention is an immunosuppressant binding protein, it can effectively be used, for example, in elucidating the mechanism of immunosuppression in living bodies, developing or screening out therapeutic agents for autoimmune diseases (e.g. rheumatism, SLE (systemic lupus erythematodes), etc.), searching for endogenous ligands to the novel binding protein and developing therapeutic agents therefor.

In the following, the gene of the present invention will be described in more detail. The gene of the present invention can be isolated by general genetic engineering techniques, for example, by selecting an appropriate clone from among a human fetal brain cDNA library (cDNA synthesized in the conventional manner from mRNA isolated and purified from total RNA obtained in turn from appropriate origin cells containing a gene coding for the FK506 binding protein) using appropriate probes, purifying said clone, and determining the base sequence thereof. In this way, the gene of the present invention can be obtained.

In the above procedure, the origin cells may be any animal cells or tissues where the occurrence of an FK506 binding protein is known, or soluble fractions of cultured cells derived therefrom. This can be isolated and purified for the culture supernatant by various chromatographic processes.

Said origin cells capable of FK506 binding protein expression can be cultured by the conventional culture method using an appropriate cell culture medium. Examples of the medium that can be used in this case are RPMI 1640 medium, CEM medium, CMRL-1066 medium, Dulbecco's modified Eagle's minimum essential medium (Eagle's MEM), Fisher's medium, F-10 medium and the like. Where appropriate, serum, such as fetal calf serum (FCS), and/or serum components, such as albumin, may adequately be added to these medium. Cultivation can be carried out in the conventional manner, for example by the carbon dioxide incubator method, generally at about 30 to 40° C., preferably at about 37° C., for about 5 to 17 days, preferably for about 8 to 11 days.

Separation of total RNA from said cultured cells or tissues can be effected by a conventional extraction method. This extraction procedure is preferably carried out at a due time when the FK506 binding protein production and accumulation in the culture supernatant resulting from the above-mentioned culture is maximal. Total RNA extraction from said origin tissue or cultured cells can be carried out as follows. When an origin tissue is used, the tissue is disrupted in an appropriate buffer solution, such as potassium phosphate buffer, supplemented with EDTA, DTT (dithiothreitol) or the like, under ice cooling, then partially or completely disrupted and solubilized by using a guanidine-isocyanate mixed solution or an appropriate surfactant such as SDS, NP-40, Triton X-100 or deoxycholic acid, or by physical means such as a homogenizer or freezing and thawing and, thereafter, chromosomal DNA is cut to a certain extent using a Polytron mixer (Kinematica, Switzerland) or a like mixer or a syringe, followed by separation into a protein fraction and a nucleic acid fraction. For the last-mentioned procedure, in particular, phenol-chloroform extraction or the cesium chloride density gradient method using ultracentrifugation at about 100,000×g [Chirgwin, J. M., et al., Biochemistry, 18, 5294 (1979)], among others, can be generally employed. In each of the processes mentioned above, it is advisable to prevent RNA decomposition otherwise caused by RNase by adding an RNase inhibitor, such as heparin, polyvinylsulfuric acid, diethyl pyrocarbonate, vanadium complex, bentonite, macaloid or the like.

Separation and purification of mRNA from the RNA obtained by the above-mentioned extraction process can be carried out, for example by subjecting the extract to an adsorption column, such as an oligo(dT)-cellulose (Collaborative Research Inc.), poly(U)-Sepharose 2B (Pharmacia) or Sepharose (Pharmacia) column, or by a batch method.

The purified mRNA obtained as mentioned above is generally unstable. Therefore, it is reversely transcribed to the stable complementary DNA (cDNA) form and the latter is joined to a replicon of the microorganism origin for enabling amplification of the desired gene. The above-mentioned in vitro transcription of mRNA to cDNA, namely cDNA synthesis, can be carried out generally in the following manner.

First, using oligo(dT) (either free oligo(dT) or oligo(dT) already joined to a vector primer) as primer, and the mRNA as template, single-stranded CDNA complementary to the mRNA is synthesized based on the latter using reverse transcriptase in the presence of dNTPs (DATP, dGTP, dCTP and dTTP). The next step differs depending on whether free oligo(dT) is used or oligo(dT) joined to a vector primer is used, as follows.

In the former case, the mRNA used as template is removed by decomposition with alkali treatment, for instance, and, then, double-stranded DNA is produced using the single-stranded DNA as template, together with reverse transcriptase or DNA polymerase. Both ends of the thus-obtained double-stranded DNA are treated with exonuclease, and an appropriate linker DNA or a plurality of bases whose combination allows annealing is joined to each, followed by insertion into an appropriate vector. This can be carried out, according to the vector used, by a conventional method, for example by the Gubler-Hoffman method. For the above-mentioned cDNA synthesis, a commercially available cDNA synthesis kit may also be used. The use of such a kit is advantageous in that the procedure becomes simple and easy. The vector to be used here is not limited to any particular species. It is recommendable, however, to select it suitably from among λgt phage vectors, EK plasmid vectors and the like, either singly or in combination, according to the host to be used. As the λgt phage vectors, there may be mentioned λgt10, λgt11, etc. The process dealing with these λgt phage vectors can be carried out by the method of Young et al. [Young, R. A., et al., in DNA Cloning, 1, 49 (1985)].

In the latter case, while the mRNA used as template is retained, the mRNA-cDNA hybrid, a linearized plasmid with a plurality of bases combined so as to enable annealing as mentioned above, and a linker DNA (often used is a DNA fragment containing a region capable of autonomous replication in animal cells and a transcription promoter region of mRNA) are together subjected to annealing to give a circularized product. Then, the mRNA is replaced with a DNA chain in the presence of dNTPs, RNase H and DNA polymerase I, to give a completed plasmid DNA.

The DNA obtained in the above manner can be introduced into an appropriate host of the vector, for example *Escherichia coli, Bacillus subtilis, Saccharomvces cerevisiae* or the like, to thereby transform the host. Employable for this DNA introduction into host for transformation are those methods that are generally used, for example the method comprising collecting cells mostly at the logarithmic growth phase, treating them with $CaCl_2$ to place in a condition suited for ready spontaneous taking up of the DNA, and allowing the plasmid to be taken up. In the above process, $Mgcl_2$ or RbCl mayor RbCl may be caused to be present so that the transformation efficiency can be further improved, as is generally known. It is also possible to employ the method comprising converting microbial cells to spheroplasts or protoplasts, followed by subjecting these to transformation. Details of these methods are described by Gubler and Hoffman [Gubler, U. and Hoffman, B. J., Gene, 25, 263 (1983)]. In cases where λ phage, which is generally and quite often used as a phage vector, is used, a cDNA library in X phage can be constructed by in vitro packaging. Commercially available cDNA libraries, for example various cDNA libraries available from Clontech, can also be used as said CDNA library.

Screening of the thus-obtained cDNA library for the gene of the present invention can be performed in the conventional manner. Thus, as the screening method, there may be mentioned, for example, the method comprising selecting the corresponding cDNA clone by Western blotting using an antibody specific to the FK506 binding protein against the protein produced by cDNA, the Southern blotting method which uses a probe selectively binding to the desired DNA sequence, the Northern blotting method, and the combination of these. As regards the probe to be used here, DNA sequences or the like chemically synthesized based on the information concerning the desired DNA or RNA sequence or the amino acid sequence encoded thereby are generally used, among others. DNA or RNA derived from the nature can also be used as such a probe.

In more detail, the above-mentioned probe is prepared in the following manner. Thus, using an oligo(dT)-cellulose column, poly(A)$^+$RNA is selected from among RNA obtained from a tissue or cultured cells containing the FK506 binding protein, single-stranded cDNA is synthesized by the method mentioned above and, after the reaction is terminated, the single-stranded cDNA is amplified by the PCR method [Saiki, R. K., et al., Science, 230, 1350–1354 (1985)] using primers estimably corresponding to information about the amino acid sequence of parts of the FK506 binding protein using an automatic oligonucleotide synthesizer.

Then, the amplified cDNA fragment is isolated and purified by 1.0% agarose gel electrophoresis. The base sequence of the thus-obtained DNA fragment can be determined in the conventional manner. For example, after the DNA fragment obtained is digested with an appropriate restriction enzyme, sequencing can be performed by the dideoxy method [Sanger, F., Nicklen, S. and Coulson, A. R., DNA sequencing with chain-terminating inhibitors, Proc. Natl. Acad. Sci. USA, 74, 5463–5467 (1977)] or the Maxam-Gilbert method [Maxam, A. M. and Gilbert, W., Methods in Enzymology, 65, 499 (1980)], for instance. Furthermore, said base sequence determination may also be readily carried out using commercially available sequencing kits or the like.

The thus-determined full-length base sequence of a DNA containing the gene of the present invention is as shown in the sequence listing under SEQ ID NO:3.

In the practice of the present invention, it is also possible to use a part of the DNA fragment sequenced in the above manner as a probe, label this using a random prime DNA labeling kit (available from Takara Shuzo, Amersham, etc.) in accordance with the random prime DNA labeling method [Feinberg, A. P., et al., Anal. Biochem., 137, 266–267 (1984)], for instance, and use the thus-obtained labeled probe in screening out the desired FK506 binding protein gene.

Using the above-mentioned labeled probe, for instance, the desired DNA can be screened out by the laque hybridization technique developed by Benton and Davis [Benton, W. and Davis, R., Science, 196, 383–394 (1977)].

The gene of the present invention as obtained in the above manner can be cloned in various plasmids in the conventional manner. For instance, after cleavage with an appropriate restriction enzyme and purification, the gene of the present invention can be inserted into a cloning vector (e.g. plasmid) cleaved with the same restriction enzyme and purified, at the cleavage site thereof, whereby a recombinant plasmid can be obtained. By introducing said recombinant into an appropriate host (e.g. Escherichia coli) for transformation, a restriction enzyme map of the clone containing said gene can be drawn using the transformant by a conventional known method, for example the method described in Molecular Cloning (A Laboratory Manual), T. Maniatis, E. F. Fritsch and J. Sambrook, Cold Spring Harbor Laboratory (1982), pages 104–106. After digestion of the above clone with an appropriate restriction enzyme, the base sequence of said clone can be determined by the above-mentioned dideoxy method or the Maxam-Gilbert method, for instance. The base sequence determination mentioned above may also be readily performed using a commercially available kit or the like.

The thus-determined DNA base sequence of the FK506 binding protein gene of the present invention and the corresponding amino acid sequence encoded thereby are as shown in the sequence listing under SEQ ID NO:1 and SEQ ID NO:2.

Using the above-mentioned gene (DNA) of the present invention, the recombinant FK506 binding protein can be obtained by various known gene recombination techniques [cf. for example Science, 224, 1431 (1984); Biochem. Biophys. Res. Comm., 130, 692 (1985); Proc. Natl. Acad. Sci. USA, 80, 5990 (1983)].

Said FK506 binding protein is produced, in more detail, by constructing a recombinant DNA allowing expression of the gene of the present invention in host cells, introducing this into host cells for transformation thereof, and cultivating the transformant strain. The host cells may be either eukaryotic or prokaryotic. As an expression vector for use with vertebrate cells, it is possible to use one containing a promoter generally located upstream of the gene to be expressed, an RNA splicing site, a polyadenylation site and a transcription termination sequence and so on. This may further have a replication origin, as necessary. Yeasts are often and generally used as eukaryotic microorganisms and, among them, yeasts belonging to the genus Saccharomyces are advantageously used. Usable as expression vectors for use with said yeasts and other eukaryotic microorganisms are pAM82 [A. Miyanohara et al., Proc. Natl. Acad. Sci. USA, 80, 1–5 (1983)] containing a promoter for the acid phosphatase gene, and like vectors. *Escherichia coli* and *Bacilus subtilis* are generally and very often used as prokaryotic host cells. When these are used as hosts in the practice of the present invention, an expression plasmid is preferably used which is derived, for instance, from a plasmid vector capable of replication in said host microorganisms and provided with a promoter, the SD (Shine and Dalgarno) base sequence and further an initiation codon (e.g. ATG) necessary for the initiation of protein synthesis, upstream from the gene of the present invention so that said gene can be expressed. As the hose *Escherichia coli* mentioned above, the strain *Escherichia coli* K12 and the like are often used and, as the vector, pBR322 is generally and often used. However, the host and vector are not limited thereto, but other various known microbial strains and vectors can also be used. As regards the promoter, the tryptophan (trp) promoter, 1 pp promoter, lac promoter and $P_L$ promoter, for instance, can be used.

The thus-obtained desired recombinant DNA can be introduced into host cells for transformation thereof by various conventional methods. The transformant obtained can be cultivated in the conventional manner, leading to production and accumulation of the desired FK506 binding protein encoded by the gene of the present invention. The medium to be used in said cultivation can adequately be selected, according to the host cells employed, from among various media in common use. When *Escherichia coli* or like cells are used as host cells, for instance, transformant cultivation can be conducted using LB medium, E medium, M9 medium, M63 medium or the like. To these media, there may be added, as necessary, generally known various carbon sources, nitrogen sources, inorganic salts, vitamins, nature-derived extracts, physiologically active substances, etc. The above-mentioned transformant cultivation can be carried out under conditions suited for the growth of the host cells. In the case of *Escherichia coli*, such conditions can be employed, for instance, as a pH of about 5 to 8, preferably 7 or thereabout, and a temperature of about 20 to 43° C., preferably 37° C. or thereabout. In the above manner, the transformant cells produce and accumulate intracellularly or secrete extracellularly the desired recombinant FK506 binding protein.

Said desired protein can be isolated and purified by various separation techniques utilizing its physical, chemical and other properties [cf. for example "Seikagaku (Biochemistry) Data Book II", pages 1175–1259, 1st edition, 1st printing, published Jun. 23, 1980 by Kabushiki Kaisha Tokyo Kagaku Dojin; Biochemistry, vol. 25, No. 25, 8274–8277 (1986); Eur. J. Biocehm., 163, 313–321 (1987)]. As specific examples of said techniques, there may be mentioned conventional reconstitution treatment, treatment with a pretein precipitating agent (salting out), centrifugation, osmotic pressure shock treatment, ultrasonic disruption, ultrafiltration, various liquid chromatographic processes such as molecular sieve chromatography (gel filtration), adsorption chromatography, ion exchange chromatography, affinity chromatography and high performance liquid chromatography (HPLC), dialysis, and combinations of these. In the above manner, the desired recombinant protein can be produced on an industrial scale with ease and with high efficiency.

BEST MODES FOR CARRYING OUT THE INVENTION

Examples will be described below to illustrate the present invention in more detail.

EXAMPLE 1

(1) Cloning and sequencing

From a human fetal brain cDNA library (Clontec, CA; Uni-ZapII vector), a 1.0 kb clone highly homologous to the human FK506 binding protein 12 kDa was selected in the conventional manner and designated OTK4.

Using the above-mentioned OTK4 as probe, the same CDNA library (about 1 million plaques) was screened, and two further cDNA clones designated OTK4(6-1) and OTK4 (4-1), respectively, were obtained. The DNA sequence of each of these three cDNA clones was determined by the dideoxy termination method using $^{32}$S-dTTP.

As a result, it was revealed that OTK4 and OTK4(6-1) have one and the same nucleic acid sequence. The full nucleic acid sequence of OTK4(6-1) is as shown in the sequence listing under SEQ ID NO:3.

This clone has an open reading frame consisting of a sequence of 324 nucleic acid residues coding for the 108 amino acid residues shown under SEQ ID NO:1. Its 5' noncoding region comprising a sequence of 72 bases contains a GC-rich sequence and its 3' noncoding region comprising a sequence of 470 bases contains the polyadenylation signal AATAAA, followed by a poly(A) tail.

On the other hand, the other clone OTK4(4-1) encodes the 80 amino acid residues represented by SEQ ID NO:2 and this is supposed to be a form derived from OTK4(6-1) by splicing. Said OTK4(4-1) has a sequence of 45 bases coding for 14 amino acid residues and the termination codon as inserted in the coding region of OTK4(6-1) at a site of the 199th base (behind Ala at position 66) and, as a result, codes for the above-mentioned 80 amino acid residues.

Comparison based on the structural analysis of FKBP-12 [Van Duyne, G. D. et al., Science, 252, 839–842 (1991)] revealed that OTK4(4-1), as compared with OTK4(6-1) having five beta-sheets, is lacking, in its C-terminal region, two beta-sheets and one loop between said sheets.

Figure 1:
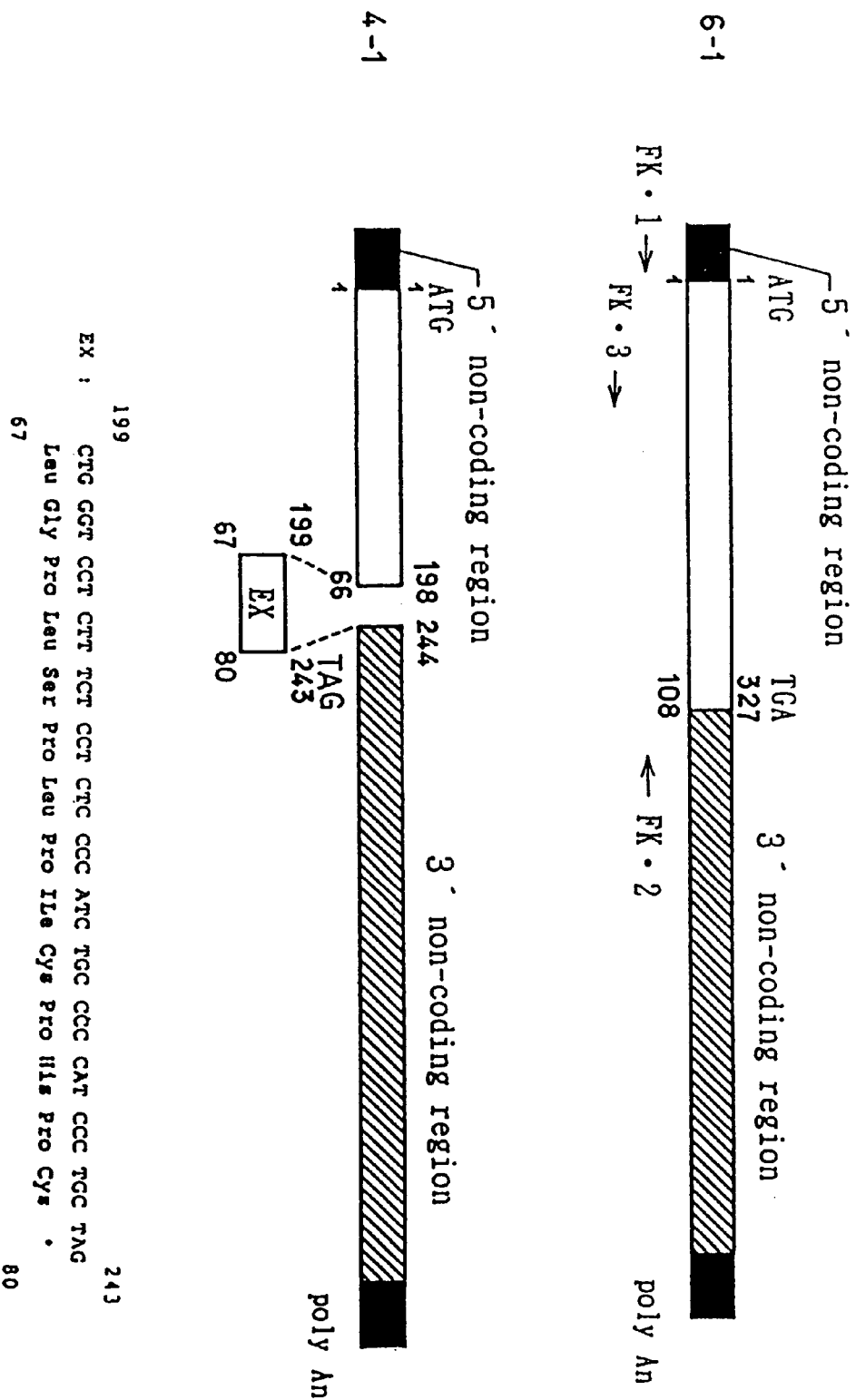
FIG. 1 schematically shows the base sequence of OTK4 (6-1) (top) and that of OTK4(4-1) (bottom).

Both of the above clones are schematically shown in FIG. 1. In the figure, arrows indicate the PCR primers FK-1, FK-2 and FK-3 to be later mentioned herein, and "EX" indicates the insertion region of the above-mentioned sequence of 45 bases.

(2) Homology with other FKBPs

OKT4(6-1) showed the highest homology with human FKBP-12. Thus, its homology with human FKBP-12 was found to be 76% in terms of nucleic acid sequence and 88% in terms of amino acid sequence.

Furthermore, it showed 49.5% (97 amino acid residues) homology, 44.6% (92 amino acid residues) homology and 38.0% (108 amino acid residues) homology with human FKBP-52 [Peattie, D. A. et al., Proc. Natl. Acad. Sci. USA, 89, 10974–10978 (1992)], FKBP-13 [Jin, Y. et al., Proc. Natl. Acad. Sci. USA, 88, 6677–6681 (1991)] and FKBP-25 [Wiederrecht, G. et al., Biochem. Biophys. Res. Comm., 185, 298–303 (1992)], resepctively.

(3) Recombinant protein production

The full coding redion of the OTK4(6-1) cDNA was amplified by the PCR method using, as primers, FK-1 and FK-2 shown below, which have a BamHI site.

TABLE 1

| Primer | Base sequence |
| --- | --- |
| FK-1 (SEQ ID NO:4) | 5'-GTGGATCCGCTATGGGCGTGGAGAT-3' |
| FK-2 (SEQ ID NO:5) | 5'-AAGGATCCGTCCCAGTGGCAGACAG-3' |
| FK-3 (SEQ ID NO:6) | 5'-TGATTCATCCAGAGACAGAA-3' |

The PCR product was digested with BamHI and cloned in the PGEX2T expression vector (Pharmacia) at its BamHI site.

The recdombinant FK506 binding protein (OTK4 protein) of the present invention was produced and purified by causing it to be expressed as a GST-fused protein in *Escherichia coli* DH5 according to the method described in the literature [Ayer, D. E. et al., Cell, 72, 211–222 (1993)].

Thus, a colony of the *Escherichia coli* strain transformed with the PGEX2T expression vector obtained as mentioned above was inoculated into 20 ml of LB/ampicillin medium and incubated at 37° C. for 12 to 15 hours.

The culture was diluted (1:10) with 200 ml of fresh LB/ampicillin medium. After 1 hour of incubation, IPTG was added (1 mM) and incubation was further continued for 3 to 5 hours. Cells were pelleted at 3,000 rpm, resuspended in 5 ml of cold lysis buffer, lysed by sonication and then incubated on ice for 1 hour. The cell lysate was centrifuged at 3,000 rpm, and the supernatant was added to Glutathion Sepharose 4B (Pharmacia) and incubated at 4° C. for 1 hour. The mixture was centrifuged at 300 rpm for 5 minutes and the supernatant was discarded. The Glutathione Sepharose 4B was washed three times with PBS and once with PBS-T (PBS containing 1% Triton X).

To obtain the full length OTK4 protein without the GST tag, the GST-fused protein was cleaved with thrombin. The Glutathione Sepharose 4B was washed with washing buffer (50 mM Tris-HCl (pH 7.5)/150 mM NaCl), 900 ml of thrombin cleavage buffer (washing buffer containing 2.5 mM $CaCl_2$) and 100 ml of thrombin (Sigma) were added to the Glutathione Sepharose 4B, and the mixture was incubated at 25° C. for 1 hour and then centrifuged at 300 rpm. The thus-obtained OTK4 protein (supernatant) was stored at −80° C.

(4) SDS-PAGE, Coomassie blue staining and protein assay

The OTK4 protein was electrophoresed on a 15% polyacrylamide gel and then analyzed by Coomassie brilliant blue staining [Wilson, C. M. et al., Methods Enzymol., 91, 236–247 (1983)].

Figure 2:
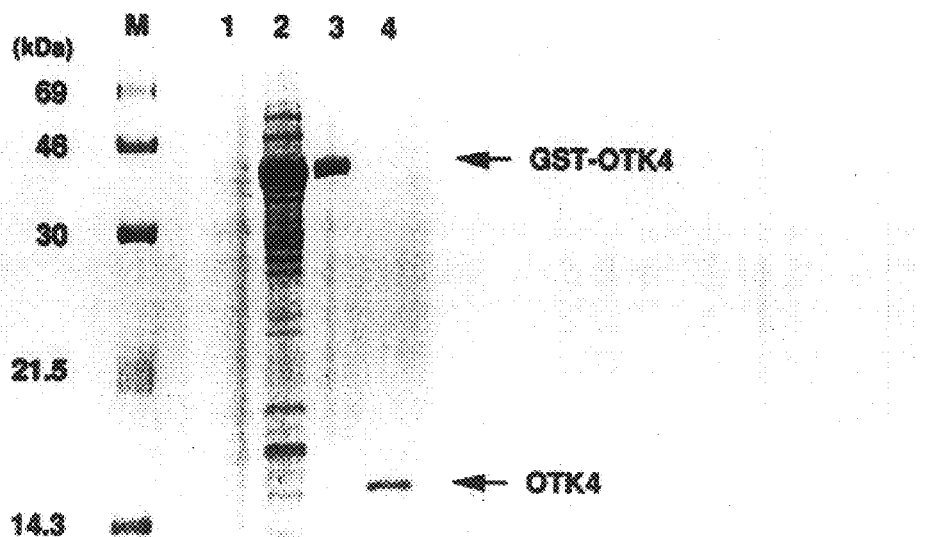
FIG. 2 shows the results of analysis of the OTK4 protein by SDS-PAGE.

The results are shown in FIG. 2. In FIG. 2, lane 1 is for the total cell protein obtained without the above-mentioned IPTG induction; lane 2 is for the total cell protein obtained with said IPTG induction; lane 3 is for the GST-OTK4 fusion protein after purification treatment; and lane 4 is for the OTK4 protein after cleavage treatment.

The OTK4 protein purified in the above manner was quantitated by the Lowry method [Lowry, O.H. et al., Nature, 337, 476–478 (1989)] to be 500 mg protein per ml.

(5) Demonstration of PPIase activity

The enzyme activity of the purified protein was determined by the method described in the literature [Fisher, G. et al., Nature, 337, 476–487 (1989)] as modified to measure the isomerization (cis to trans) of the proline-alanine peptide bond in the peptide (N-succinyl-Ala-Ala-Pro-Phe-p-nitroanilide).

The trans form of the above peptide is readily cleaved with chymotrypsin, releasing p-nitroanilide which can be quantitated by absorbance measurement at 405 nm.

The reaction mixture (1.0 ml) contained the above-mentioned peptide substrate (30 µl taken from a 2.1 mM stock solution; final concentration 0.1 mM), 100 mM Tris-HCl (pH 7.8) and 1.0 µg/ml or 10 µg/ml of the OTK4 protein, and the reaction was carried out at 25° C.

One minute later, 30 µl of 100 mM Tris-HCl (pH 7.8) containing 2 mg/ml of chymotrypsin (Sigma) was added and mixed. Ten seconds after the mixing and thereafter, the absorbance at 405 nm was measured on a spectrophotometer at 10-second intervals.

Figure 3:
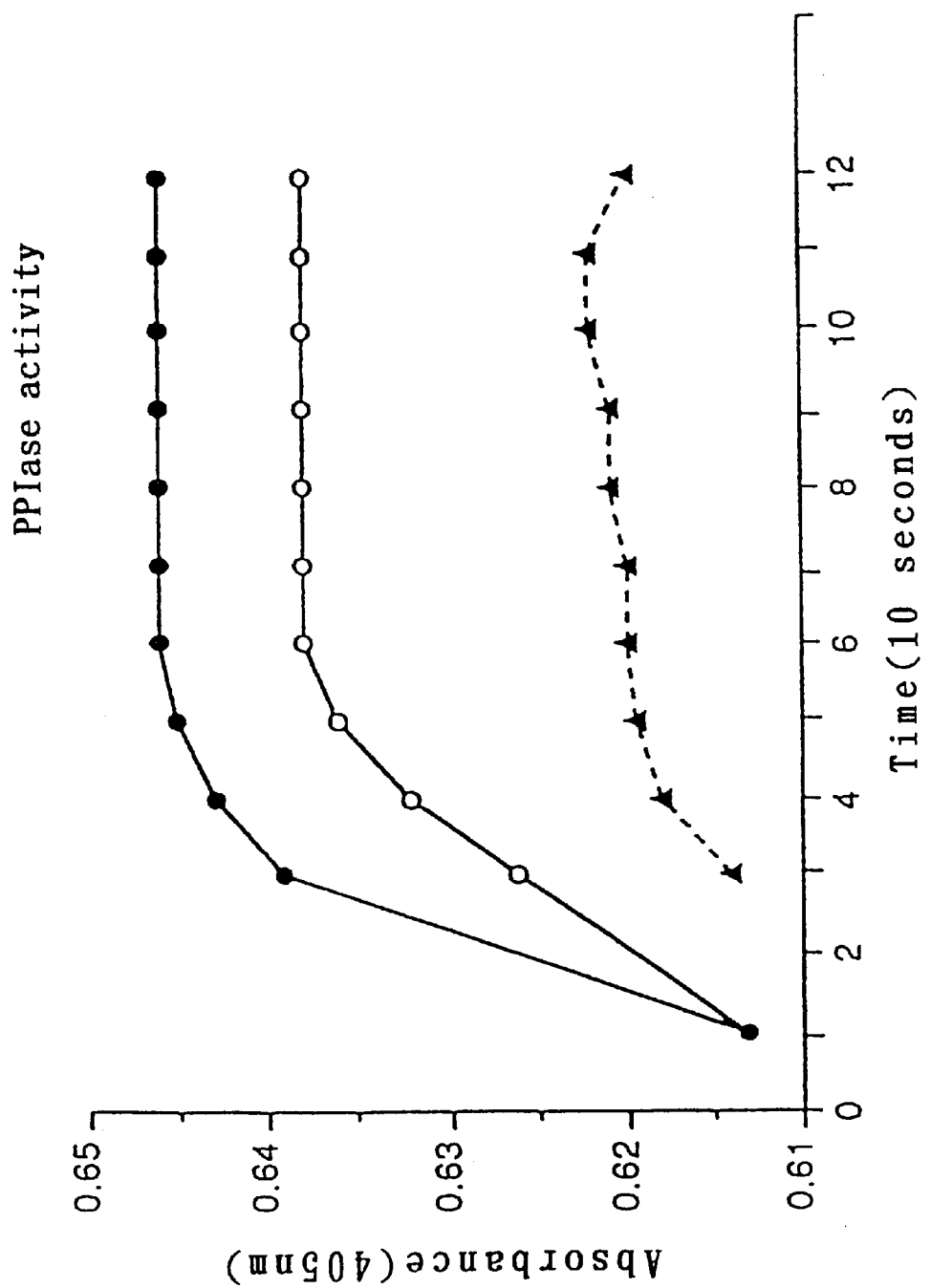
FIG. 3 shows the PPIase activity of the OTK4 protein.

The results obtained are shown in FIG. 3 [ordinate =absorbance (405 nm); abscissa=time (×10 seconds)]. In FIG. 3, the curve containing open circles indicates the results obtained with 1.0 gg/ml of OTK4 protein; the curve containing closed circles indicates the results obtained with 10 µg/ml of OTK4 protein; and the curve containing closed triangles indicates the results obtained with a control without OTK4 protein.

As seen in said figure, a marked increase in absorbance were observed in the OTK4 protein groups as compared with the control, and activity levels dependent on the dose of OTK4 protein were observed.

(6) Northern Blot Analysis of Various Organs Levels of expression of the OTK4 gene in various tissues were examined using Clontec's mRNA (human multiple tissue Northern blot system).

Thus, 4 hours of prehybridization and 18 hours of hybridization were carried out at 50° C. in a solution containing 50% formamide, 10×Denhardt's solution, 5×SSPE, 2% SDS and 100 µg of denatured salmon sperm DNA.

The probe used was $^{32}$P-labeled OTK4 cDNA. Washing was performed with 2×SSC/0.05% SDS at room temperature for 10 minutes (three times) and then with 0.1×SSC/ 0.1% SDS at 50° C. for 15 minutes (two times), followed by 60 hours of exposure at −80° C.

Figure 4:
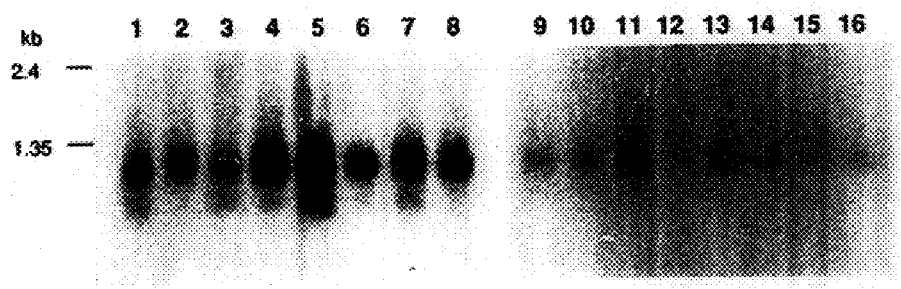
FIG. 4 shows the results of Northern blot analysis of various tissues using the OTK4 gene.

The results are shown in FIG. 4. In the figure, lane 1 and the succeeding lanes correspond, in that order, heart, brain, placenta, lung, liver, skeletal muscle, kidney, pancreas, spleen, thymus, prostate, testis, ovary, small intestine, colon and peripheral blood leukocyte. On the utmost left, there are shown mRNA size markers (in kb).

From said figure, it is evident that OTK4 gene mRNA expression is observable in various tissues.

(7) RT (reverse transciptase)-PCR Analysis of Various Organs

Using the random primer $p(dN)_6$ (Boehringer Mannheim GmbH), 10 µg of each organ RNA was reverse-transcribed, followed by amplification by PCR using the primers FK-1 and FK-2 (cf. Table 1). The PCR reaction conditions were as follows: 40 cycles with the regime: 94° C. for 0.5 minute, 54° C. for 1 minute, and 72° C. for 1 minute per cycle.

In the conventional manner, each product was then subjected to 2% agarose gel electrophoresis, transferred to a nylon membrane, and hybridized at 50° C. with terminally $^{32}$P-labeled FK-3 (cf. Table 1). After washing with 6×SSC at room temperature for 10 minutes and further at 50° C. for 10 minutes, the membrane was autoradiographed for detection, with acting as control.

Figure 5:
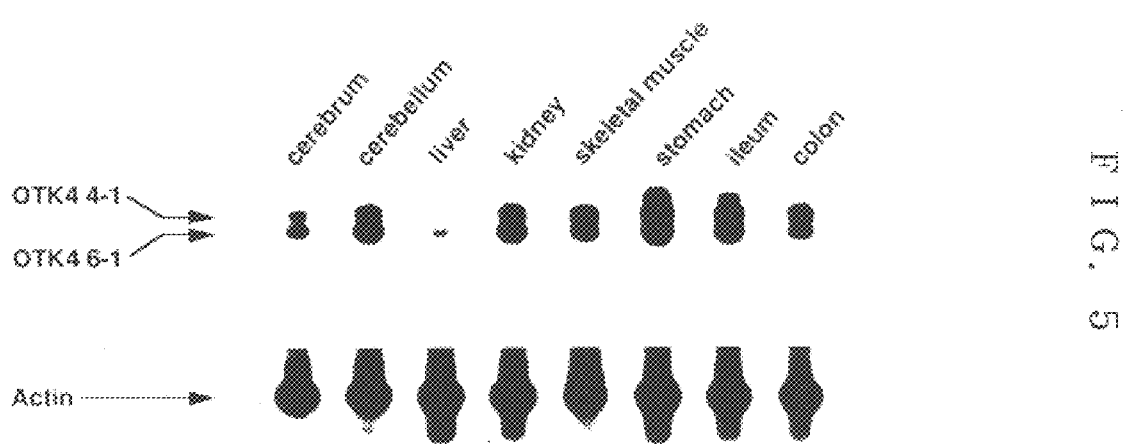
FIG. 5 shows the results of RT-PCR analysis of various tissues to investigate the expression of OTK4(4-1) and OTK4(6-1).

The results thus obtained are shown in FIG. 5.

The following or agns were used:

cerebrum, cerebellum, liver, kidney, skeletal muscle, stomach, ileum and colon.

From said figure, it is evident that both OTK4(4-1) and OTK4(6-1) are expressed ubiquitously although the expression of OTK4(4-1) is superior to that of OTK4(6-1).

INDUSTRIAL APPLICABILITY

The present invention provides an FK506 binding protein gened. The use of said gene makes it possisble to produce the FK506 binding protein with ease and in large quantities, and said protein, which has PPIase activity, can be used in developing therapeutic agents for various diseases.

What is claimed is:

1. An isolated purified FK506 binding protein gene which comprises bases 70–393 of SEQ ID NO:3.

2. A method of producing a recombinant FK506 binding protein which comprises introducing a base sequence containing the FK506 binding protein gene of claim 1 into a host to thereby transform said host, cultivating the thus-obtained transformant, and recovering the recombinant FK506 binding protein thus produced.

3. An expression vector which contains a gene as claimed in claim 1.

4. A host cell which is transformed with a vector as claimed in claim 3.

5. A recombinant FK506 binding protein produced by the method as claimed in claim 2.

6. An isolated and purified FK506 binding protein gene which comprises a base sqeuence coding for the amino acid sequence of SEQ ID NO:2.

7. An expression vector which contains a gene as claimed in claim 6.

8. A host cell which is transformed with a vector as claimed in claim 7.

9. A method of producing a recombinant FK506 binding protein which comprises introducing a base sequence containing the FK506 binding protein gene of claim 6 into a host to thereby transform the host, cultivating the thus-obtained transformant, and recovering the recombinant FK506 binding protein thus produced.

10. A recombinant FK506 binding protein which has the amino acid sequence of SEQ ID NO:2.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
       (A) LENGTH: 108 amino acids
       (B) TYPE: amino acid
       (D) TOPOLOGY: linear (ii) MOLECULE TYPE: protein (xi) SEQUENCE DESCRIPTION: SEQ ID NO:1:

```
Met Gly Val Glu Ile Glu Thr Ile Ser Pro Gly Asp Gly Arg Thr Phe
 1               5                  10                  15

Pro Lys Lys Gly Gln Thr Cys Val Val His Tyr Thr Gly Met Leu Gln
            20                  25                  30

Asn Gly Lys Lys Phe Asp Ser Ser Arg Asp Arg Asn Lys Pro Phe Lys
            35                  40                  45

Phe Arg Ile Gly Lys Gln Glu Val Ile Lys Gly Phe Glu Glu Gly Ala
        50                  55                  60

Ala Gln Met Ser Leu Gly Gln Arg Ala Lys Leu Thr Cys Thr Pro Asp
65                  70                  75                  80

Val Ala Tyr Gly Ala Thr Gly His Pro Gly Val Ile Pro Pro Asn Ala
                85                  90                  95

Thr Leu Ile Phe Asp Val Glu Leu Leu Asn Leu Glu
            100                 105
```

(2) INFORMATION FOR SEQ ID NO:2:

(i) SEQUENCE CHARACTERISTICS:
       (A) LENGTH: 80 amino acids
       (B) TYPE: amino acid
       (D) TOPOLOGY: linear (ii) MOLECULE TYPE: protein (xi) SEQUENCE DESCRIPTION: SEQ ID NO:2:

```
Met Gly Val Glu Ile Glu Thr Ile Ser Pro Gly Asp Gly Arg Thr Phe
 1               5                  10                  15

Pro Lys Lys Gly Gln Thr Cys Val Val His Tyr Thr Gly Met Leu Gln
            20                  25                  30

Asn Gly Lys Lys Phe Asp Ser Ser Arg Asp Arg Asn Lys Pro Phe Lys
            35                  40                  45

Phe Arg Ile Gly Lys Gln Glu Val Ile Lys Gly Phe Glu Glu Gly Ala
        50                  55                  60

Ala Gln Leu Gly Pro Leu Ser Pro Leu Pro Ile Cys Pro His Pro Cys
65                  70                  75                  80
```

(2) INFORMATION FOR SEQ ID NO:3:

(i) SEQUENCE CHARACTERISTICS:
       (A) LENGTH: 879 base pairs
       (B) TYPE: nucleic acid
       (C) STRANDEDNESS: single
       (D) TOPOLOGY: linear (ii) MOLECULE TYPE: cDNA (iii) HYPOTHETICAL: NO (iv) ANTI-SENSE: NO (vi) ORIGINAL SOURCE:
             (A) ORGANISM: Human fetal brain cDNA library (vii) IMMEDIATE SOURCE:
             (B) CLONE: OTK4(6-1)

(ix) FEATURE:
             (A) NAME/KEY: CDS
             (B) LOCATION: 70..393

(xi) SEQUENCE DESCRIPTION: SEQ ID NO:3:

```
CGCTGGGCCG GAGCCGAGCC GGGGTCGGGC AGCAGCAGGA CCCCCAGAGG CGGGGCCTGT      60

GGGACCGCT ATG GGC GTG GAG ATC GAG ACC ATC TCC CCC GGA GAC GGA         108
          Met Gly Val Glu Ile Glu Thr Ile Ser Pro Gly Asp Gly
            1               5                  10

AGG ACA TTC CCC AAG AAG GGC CAA ACG TGT GTG GTG CAC TAC ACA GGA       156
Arg Thr Phe Pro Lys Lys Gly Gln Thr Cys Val Val His Tyr Thr Gly
 15                  20                  25

ATG CTC CAA AAT GGG AAG AAG TTT GAT TCA TCC AGA GAC AGA AAC AAA       204
Met Leu Gln Asn Gly Lys Lys Phe Asp Ser Ser Arg Asp Arg Asn Lys
 30                  35                  40                  45

CCT TTC AAG TTC AGA ATT GGC AAA CAG GAA GTC ATC AAA GGT TTT GAA       252
Pro Phe Lys Phe Arg Ile Gly Lys Gln Glu Val Ile Lys Gly Phe Glu
                 50                  55                  60

GAG GGT GCA GCC CAG ATG AGC TTG GGG CAG AGG GCG AAG CTG ACC TGC       300
Glu Gly Ala Ala Gln Met Ser Leu Gly Gln Arg Ala Lys Leu Thr Cys
                     65                  70                  75

ACC CCT GAT GTG GCA TAT GGA GCC ACG GGC CAC CCC GGT GTC ATC CCT       348
Thr Pro Asp Val Ala Tyr Gly Ala Thr Gly His Pro Gly Val Ile Pro
                         80                  85                  90

CCC AAT GCC ACC CTC ATC TTT GAC GTG GAG CTC CTC AAC TTA GAG           393
Pro Asn Ala Thr Leu Ile Phe Asp Val Glu Leu Leu Asn Leu Glu
                 95                 100                 105

TGAAGGCAGG AAGGAACTCA AGGTGGTGGC TGGAGATGGC TGCTGCTCAC CCTCCTAGCC     453

TGCTCTGCCA CTGGGACGGC TCCTTGCTTT TGGGGCTCTT GATCAGTGTG CTAACCTCAC     513

TGCCTCATGG CATCATCCAT TCTCTCTGCC CAAGTTGCTC TGTATGTGTT CGTCAGTGTT     573

CATGCGATTC TTGCTTGAGG AAACTTCGTG CAGATTAAGC ATTCAAGGTT GTGCATTTTG     633

TGTGATGCAG TAGTAGCCTT TCCTGATAAC AGAACACAGA TCTCTTGTTC GCACAATCTA     693

CACTAGCCAT TACCTTCACA TTAAACCACA CACAAGGTGC TCAGACATGA AATGTACATG     753

GCGTACCGTA CACAGAGGGA CTTGAGCCAG TTACCTTTGC TGTCACTTTC TCTCTTATAA     813

ATTCTGTTAG CTGCTCACTT AAACAATGTC CTCTTTGAGA AATGTAAAA TAAAGGCTCT      873

GAGCTT                                                                879
```

(2) INFORMATION FOR SEQ ID NO:4:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

```
GTGGATCCGC TATGGGCGTG GAGAT                                            25
```

-continued (2) INFORMATION FOR SEQ ID NO:5:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

AAGGATCCGT CCCAGTGGCA GACAG                        25

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

TGATTCATCC AGAGACAGAA                             20